United States Patent
Gurnani et al.

(10) Patent No.: US 9,394,340 B2
(45) Date of Patent: Jul. 19, 2016

(54) PURIFICATION PROCESS FOR LIPOPEPTIDES

(75) Inventors: Menka Gurnani, Gujarat (IN); Rajkumar Maurya, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 1885 days.

(21) Appl. No.: 12/729,284

(22) Filed: Mar. 23, 2010

(65) Prior Publication Data

US 2010/0249371 A1   Sep. 30, 2010

(30) Foreign Application Priority Data

Mar. 24, 2009 (IN) .......................... 676/MUM/2009

(51) Int. Cl.
*A61K 38/00* (2006.01)
*C07K 16/00* (2006.01)
*C07K 7/56* (2006.01)
*C07K 1/32* (2006.01)

(52) U.S. Cl.
CPC .... *C07K 7/56* (2013.01); *C07K 1/32* (2013.01)

(58) Field of Classification Search
None
See application file for complete search history.

(56) References Cited

U.S. PATENT DOCUMENTS 4,931,352 A * 6/1990 Fromtling et al. ............ 435/71.3
5,573,936 A * 11/1996 Kreuzman et al. ............ 435/196

OTHER PUBLICATIONS

Schwartz, Robert E., et al., "Discovery, Production Development and Isolation of Pneumocandin $B_0$", *Cutaneous Antifungal Agents*, , 1993, pp. 375-393.
Schwartz, Robert E., et al., "Pneumocandins From *Zalerion arboricola*, Discovery and Isolation", *The Journal of Antibiotics*, vol. 45, No. 12, Jun. 15, 1992, pp. 1853-1866.

* cited by examiner

*Primary Examiner* — Jeanette Lieb
(74) *Attorney, Agent, or Firm* — Ladas & Parry LLP

(57) ABSTRACT

The present invention provides simple, cost effective, rapid, and scalable at industrial scale and provide high purity and yield of Echinocandin-type compounds at low cost as compared to prior art. Moreover the process allows for the removal of impurities by using economical salt-adsorbent complex and provide highly purified Echinocandin type compounds which is highly improved in terms of purity and sufficient for further processing to obtain an active pharmaceutical ingredient such as, the antifungals caspogungin, anidulafungin, and micafungin.

17 Claims, No Drawings

PURIFICATION PROCESS FOR LIPOPEPTIDES

FIELD OF THE INVENTION

The present invention relates to the improved process for purification of lipopeptide compounds, and in particular certain Echinocandin-type compounds, by using salt-adsorbent complex complex(s). In a further embodiment, it also includes appropriate combination of solvents for binding and elution of compound from the salt-adsorbent complex complex(s).

BACKGROUND

Echinocandin lipopeptides are natural products that have shown potent fungicidal activity against *Aspergillus* and *Candida* sp. and protect animals from fungicidal infection by inhibiting the enzyme $\beta(1,3)$-D-Glucan synthase, thereby disturbing the integrity of the fungal cell wall. Echinocandin family compounds are natural products such as Echinocandin B, Echinocandin C, Mulundocandin, Sporiofungin A, Pneumocandin A0, and Pneumocandin B0. Their isolation, structure elucidation and biological evaluation have been reported by Schmartz et al in "Cutaneous Antifungal Agents, 1993, pp 375-394". The natural Echinocandin products are used as a precursor for semi-synthetic lipopeptides such as Anidulafungin, Micafungin, Caspofungin.

Anidulafungin is a semisynthetic lipopeptide Echinocandin B derivative developed by Eli Lilly/Versicor as an antifungal agent for intravenous administration. Anidulafungin is disclosed in U.S. Pat. Nos. 5,965,525 and 6,384,013, & are hereby incorporated by reference. Cilofungin is an Echinocandin lipopeptide disclosed by Eli Lilly in U.S. Pat. No. 4,293,489 for use as an antifungal agent, which is also hereby incorporated by reference. Micafungin (FUNGARD) is an Echinocandin-like lipopeptide developed by Fujisawa, as an antifungal agent for intravenous administration. Micafungin is disclosed in U.S. Pat. No. 6,107,458 which is also hereby incorporated by reference. Daptomycin (CIDECIN) is a semisynthetic lipopeptide derivative developed by Cubist as an antibacterial agent. Daptomycin is disclosed by Eli Lilly in U.S. Pat. No. 4,537,717 hereby incorporated by reference.

Pneumocandin B0 is produced as a secondary metabolite by fermentation of the fungus *Glarea lozoyensis* (U.S. Pat. Nos. 5,194,377 and 5,202,309) which is precursor for Caspofungin acetate (CANCIDAS), a semisynthetic lipopeptide Echinocandin B derivative currently being sold in US as an antifungal agent for intravenous administration.

The purification of Echinocandin lipopeptide compounds is a technical challenge despite intense research effort directed at controlling distribution and amount of various analogues produced by organism during fermentation. The organism can produce, in addition to desired compound, 20 or more Echinocandin-type compounds including Pneumocandin A0 and C0. Furthermore, these lipopeptides have unique solubility properties; they are essentially insoluble in water and most pure solvents, but dissolve in alcohols and some aqueous/organic solvent mixture. Moreover, it is difficult, if not impossible, to purify them by crystallization.

Therefore, the separation of any desired product like Pneumocandin B0 from its key analog impurities like pneumocandin C0, pneumocandin B5 and pneumocandin E0 is very cumbersome and expensive because all of them comprise a cyclic hexapeptide coupled with dimethylmyristate side chain.

Several efforts have been made to separate desired Pneumocandins from culture broth and to purify it by using various processes to obtain good productivity of highly purified Pneumocandins.

U.S. Pat. No. 4,874,843 describes the use of non-functional resin in reversed mode to purify Echinocandin-type products. Even though the process improved the purity of products derived from fermentation process, further improvements are still needed to remove contaminants that are difficult to separate from both the intermediate and final pharmaceutical compounds.

The use of SP-207, HP-20 resin and reverse phase HPLC are described for the separation of pneumocandin B0. (U.S. Pat. No. 5,162,211 and Robert E. Schwartz, The Journal of Antibiotics, Vol. 45, No. 12 1853-1866, 1992). R. E. Schwartz et. al. (1992) describe large scale whole broth methanol extract purification by use of fluidized bed of SP-207 followed by HP 20 column and then again use SP-207 for further material concentration and then purification of the same over silica column. This process has disadvantage that the purification method is very complicated because of being multi-step process. Furthermore, SP-207 and HP-20 are capital expensive to use at large scale production. Another disadvantage is that process is very time consuming and a major amount of desired product is lost in the transfer of sample from one column to another that decreases the yield of product of interest and makes the recovery of product poor.

U.S. Pat. No. 6,610,822 describes the purification process for Pneumocandin B0 where two phase, multi solvent system and back extraction steps have been used to maintain the polarity balance of the solution in which the compound is purified. The process comprises use of multiple solvents like isobutyl alcohol (IBA), methanol, n-heptane, water and acetonitrile, which is used in the extraction and purification of Pneumocandin B0. The problem associated with the said process is that recovery and reuse of multisolvent system involves critical monitoring as the process depends upon exact ratio of solvents to bring about polarity shift as described earlier. The process has low productivity, overall yield 69% and purity obtained is 61.4%.

US 2008/0108806 also describes purification of Echinocandin-type compounds such as pneumocandins, by two-phase system, first to remove non polar impurities and then extraction of compound followed by crystallization and precipitation. The first extraction is performed using non-polar or weakly polar water immiscible organic solvent followed by second extraction using water immiscible alcohols. The second extraction is followed by concentration and crystallization/precipitation. The crystallization/precipitation process by addition of antisolvent is facilitated using solid carriers. The process describes use of solid carriers to precipitate compound from the concentrated solution. This process also has low productivity.

U.S. Pat. Nos. 6,506,726 and 6,590,073 describe purification of echinocandin type compounds, especially of deacylated echinocandin B by chromatography.

EP1157030 describes formation of crystalline complex between echinocandin-type compounds and carbohydrate. The patent describes enhanced stability and water solubility for these complexes.

Since the potency of the final pharmaceutical product is dependent upon the purity of intermediates used to make the final product, therefore the improvements in purity at any stage of the manufacturing process is highly desirable. Ideally, the contaminants should be removed at the earliest stage possible in the manufacturing process.

Accordingly, conventional technologies of purifying pneumocandin B0 from the culture broth are problematic in that highly purified Pneumocandin B0 is not readily produced, stability of compound is not maintained, the recovery yield is relatively low and production cost are relatively high. Hence, there remains a long felt need to develop an improved purification process, which provides better resolution and productivity of Pneumocandins and other Echinocandin-type compounds at economical cost. Therefore, the object of the present invention is to develop an improved & economical purification process to obtain good yield and purity of certain Echinocandin-type compounds by using salt-adsorbent complex such as calcium phosphate. Moreover, the present process is simpler and provides improved productivity and purity than some of the existing process for the purification of Echinocandin-type compounds.

The present process is simple, cost effective, rapid, and scalable at industrial scale and provide highly purified yield of Echinocandin-type compounds at low cost as compared to prior art. The method allows for the removal of impurities by using economical salt-adsorbent complex and provide highly purified echinocandin type compounds which is highly improved in terms of purity than prior art and sufficient for further processing to obtain an active pharmaceutical ingredient such as, for example the antifungals caspogungin, anidulafungin, and micafungin.

Additionally this method reduces overall solvent and energy consumption making the process economically viable for commercial use and does not require chromatography steps involving expensive resins which are used in prior art processes for the isolation and purification of similar natural products.

OBJECTS OF THE INVENTION

In one embodiment, the present invention provides a simple, rapid and an efficient method for the purification of lipopeptides especially Echinocandin type compounds.

In another embodiment of the present invention provides the use of salt-adsorbent complexes to purify and recover the Echinocandin type compound from the process solvents.

In another embodiment, the present invention also reduces the related structural analogue impurities from the Echinocandin compound of interest.

In yet another embodiment the anions of the salt-adsorbent complex is selected from phosphates, carbonates and sulphates.

In yet another embodiment of the present invention describes the binding, appropriate washing and elution conditions for improved productivity.

In further embodiment the present invention provides a cost effective purification process compared to those known in the prior art.

DETAILED DESCRIPTION

The present invention provide a process, which is easily scalable, cost effective, and with improved purity.

The present invention provides a process for separation and purification of compounds related to the class of Echinocandin-type compounds. The present process is simple, cost effective, rapid, and scalable at industrial scale and provide highly purified yield of compounds at low cost. As used herein unless mentioned otherwise, the term "Compound-salt-adsorbent complex" refers to a unit where a compound is adsorbed on the salt either strongly or weakly.

As used herein unless mentioned otherwise, the term "Echinocandin-type compounds" refers to compounds which belong to Echinocandin family or share common structural features of Echinocandins or analogues of Echinocandins.

As used herein unless mentioned otherwise, the term "salt-adsorbent complex" refers to those salts which adsorb the Echinocandin-type compounds. The salts are selected from salts of phosphates, carbonates and sulphates. Preferred are those salts which are highly insoluble or weakly soluble in process solvent(s) and at least comprise one cation.

In one embodiment, the present invention provides a new process for separation and purification of lipopeptide compounds. In another embodiment, the present invention provides a new process for separation and purification of Echinocandin-type compounds. In preferred embodiment, the present invention provides a new process for separation and purification of Pneumocandins, from—fermentation broths or partially purified process streams. In such embodiment, the present invention uses suitable salt-adsorbent complex complex to bind compound from solution or whole broth which is followed by physical separation of the compound-salt-adsorbent complex from the medium comprising solution or whole broth and thereafter recovering the Echinocandin-type compounds by elution in presence of appropriate solvent system from salt adsorbent.

In one embodiment the present invention uses salt adsorbents, which adsorb the Echinocandin-type compounds. In preferred embodiment Salt-adsorbent complex are insoluble compounds and comprise at least one anion and cation.

In one embodiment the present invention uses suitable salt-adsorbent complex selected from but not limited to phosphates, carbonates and sulphates and at least comprises one cation. In preferred embodiment, the salt-adsorbent complex is calcium phosphate. In another embodiment, the salt adsorbent binds the Echinocandin-type compounds, which is followed by physical separation of the compound-salt-adsorbent complex from the medium containing solution or broth and thereafter recovered the Echinocandin-type compounds by elution in presence of appropriate solvent system from salt adsorbent.

In one embodiment, the process for separation and purification of lipopeptide compounds which are of the class of Echinocandin or are Echinocandin-type compounds, comprises following steps—
 a) addition of salt adsorbent(s), such as calcium phosphate in whole fermentation broth containing Echinocandin or Echinocandin-type compound and/or in situ formation of similar salt-adsorbent complex.
 b) separation of cake which comprise salt-compound adsorbent and mycelia;
 c) extraction of compound of interest from the cake by using suitable organic solvent(s);
 d) concentration of the solvent
 e) further addition of salt adsorbents such as calcium phosphate to bind the compound of interest from solution where compound of interest again forms salt-compound adsorbent complex;
 f) further separation of compound salt adsorbent;
 g) optionally, washing of separated compound-salt adsorbent by the using suitable washing system;
 h) elution of compound of interest from adsorbent by using appropriate eluting system;
 i) concentration of eluate;
 j) precipitation of the product.

In one embodiment, the present invention describes the process for the purification of suitable Echinocandin-type compounds preferably, Pneumocandins and its structural analogues which are selected from Pneumocandin B0, Pneumocandin A0, Pneumocandin C0, Pneumocandin D0, E0, B2 and B5. In preferred embodiment the present invention describes purification of Pneumocandin B0 from its structural analogues. However, it is to be understood that scope of the present invention is not limited to the use of a salt-adsorbent complex for the separation and purification of Pneumocandins or Echinocandin-type compounds. It can also be employed to purify other natural products in Lipopeptide family or other similar natural products.

Pneumocandin B0 is produced by the process known in the art by cultivating *Glarea losoyeinsis* (formerly identified as *Zalerion arboricola*), ATCC 74030 in a suitable nutrient medium, similar to those described in U.S. Pat. No. 5,306,708.

In one embodiment, the appropriate concentration of Pneumocandins is obtained by carrying out the fermentation process and the salt-adsorbent complex such as calcium phosphate is added in the broth.

In preferred embodiment, the salt-adsorbent complex such as calcium phosphate is formed in situ in step (a) of the process by the addition of chemicals such as calcium chloride in a phosphate containing fermentation broth.

In another preferred embodiment, salt-adsorbent complex such as calcium phosphate is added extraneously or formed in-situ during or after fermentation process.

In another embodiment of the present invention, addition or in situ formation of salt-adsorbent complex such as calcium phosphate in the fermentation whole broth helps to recover extracellularly released compounds. The process allows removing of the impurities as well as remaining medium components, which are soluble in water, and thereafter the solid cake is obtained comprising compound-salt-adsorbent complex and mycelium. Therefore, it was surprisingly found that the addition and/or formation of salt-adsorbent complex in step (a) not only prevents loss of extracellular product but also significantly reduces the processing volume. In one embodiment, the compound of interest is extracted (step c) from the above solid cake by the use of suitable solvent system.

In another preferred embodiment the Echinocandin type compound is extracted from the whole broth or compound obtained from any other stream of recovery process which are known in the art. Thereafter salt adsorbents such as calcium phosphate is added for binding of the Echinocandin type compound from solution where Echinocandin type compound of interest forms salt-compound adsorbent complex in suitable solvent system.

In one embodiment, the suitable solvents used either alone or in combination with each other are selected from but not limited to ($C_1$-$C_6$) alcohols, such as methanol, ethanol, isopropyl alcohol, isobutyl alcohol and n-butanol, preferably methanol, isobutyl alcohol; ($C_2$-$C_6$)ketones such as acetone, acetophenone, methyl ethyl ketone, methyl isopropyl ketone preferably acetone; and acetonitrile.

The extraction step (c) can be repeated to further increase the yield of compound of interest in the solvent. In one embodiment the compound of interest is obtained in the aqueous phase by evaporating the solvent, when the extraction solvent is water miscible such as methanol. In another embodiment, the compound of interest is obtained in the solvent phase by concentrating under vacuum, when the extraction solvent is water immiscible such as isobutyl alcohol or n-butanol. The compound of interest may further be purified by repeating the use of salt-adsorbent.

In another embodiment the compound is extracted from whole broth using suitable organic solvent. In one embodiment, the solvent used either alone or in combination with each other are selected from but not limited to $C_1$-$C_6$ alcohols, such as methanol, ethanol, isopropyl alcohol, isobutyl alcohol and n-butanol, preferably methanol, isobutyl alcohol; ($C_2$-$C_6$)ketones selected from acetone, acetophenone, methyl ethyl ketone, methyl isopropyl ketone preferably acetone; and acetonitrile. In preferred embodiment water immiscible organic solvent is $C_4$-$C_6$ alcohols. In most preferred embodiment, water immiscible organic solvent is isobutanol, n-butanol.

The compound of interest is further purified in step (c) by the use of the salt-adsorbent complex.

The present invention further includes but not limited to the extraction of Echinocandin type compound from the whole broth or compound obtained from any other stream of recovery process in the presence of suitable solvent selected from methanol or isobutanol and thereafter the solvent containing Echinocandin type compounds is treated with the salt adsorbents such as calcium phosphate for binding of the Echinocandin type compound from solvent where Echinocandin type compound of interest forms salt-compound adsorbent complex in suitable solvent system.

The inventors of the present invention surprisingly found that the use of salt-adsorbent complex such as calcium phosphate easily separated the compound of interest from the water/organic solvent, which makes the process simple, rapid, cost effective and provides easy recovery of solvents at industrial scale.

In another embodiment, the Echinocandin type compound is obtained from any other stream of purification process, thereafter the compound of interest is purified through appropriate salt-absorbent in the presence of suitable solvent. In such embodiment, the solvent used either alone or in combination with each other are selected from but not limited to $C_1$-$C_6$ alcohols, such as methanol, ethanol, isopropyl alcohol, Isobutyl alcohol and n-butanol, preferably methanol, isobutyl alcohol; ($C_2$-$C_6$)ketones selected from acetone, acetophenone, methyl ethyl ketone, methyl isopropyl ketone preferably acetone; and acetonitrile.

In one embodiment of the invention, the salt-adsorbent complex complex is used for adsorption of Echinocandin type compound on salt-adsorbent complex complex. In such embodiment, the anions of salts, includes but are not limited to phosphates, carbonates and sulphates. In preferred embodiment anion of salt is Phosphate. In another embodiment, the cations of the salts, include but are not limited to calcium (Ca), copper (Cu), iron (Fe), Mangese (Mn), Magnesium (Mg), Zinc (Zn), Barium (Ba). In preferred embodiment the cation of salt is calcium. In one embodiment the salt-absorbents can be synthesized chemically such as calcium phosphate or obtained naturally such as hydroxy apatite.

In preferred embodiment, anions and cations are used for in-situ formation of salt-absorbents and it further makes adequate salt-compound complex with Echinocandin type compound, preferably Pneumocandins.

In another preferred embodiment, the salt-adsorbent may be directly added to liquid containing Echinocandin type compound, in order to achieve adequate compound-salt-adsorbent complex.

In such an embodiment, the salt-absorbent are used in powder or particulate form. In preferred embodiment, powder form is used and the salt-adsorbent complex and compound adsorption process is performed (Step e) in batch or continuous mode, preferably batch mode at industrial scale.

Without wishing to be bound to any addition concentration of salt adsorbent, the addition concentration of salt adsorbent can be varied to get efficient compound-salt-adsorbent complex complex. In one embodiment at least 0.1 times or more amount of salt adsorbent quantity than measured Pneumocandin B0 is added to liquid containing Pneumocandin B0, in order to obtain adequate adsorption between salt and Pneumocandin B0. In another embodiment, at least 0.1% (w/v) or higher concentrations of the salt-absorbent is used, in preferred embodiment, at least 0.5% (w/v) of the liquid containing Pneumocandin B0. In such an embodiment, the adsorption of compound on salt-adsorbent complex starts immediately as the salt-adsorbent and compound are mixed, but the degrees of adsorption gradually increase with time. However, increasing the quantity of salt-adsorbent also decreases the time for major adsorption of compound on it.

The salt-adsorbent is mixed with Echinocandin type compounds and suitable system is obtained for optimum adsorption of Echinocandin type compounds on salt adsorbent.

In such embodiment, the selection of the suitable system depends upon the decreased solubility of compound. The system is selected from aqueous system or organic solvent or combination thereof for the formation of adequate compound-salt-adsorbent complex. The organic solvent includes both water miscible and water immiscible solvents. The solvent used are selected from but not limited to fully aqueous system or C1-C6 lower alcohols such as methanol, ethanol, isopropyl alcohol, Isobutyl alcohol and n-butanol, preferably methanol and iso butyl alcohol; ketones such as acetone, acetophenone, methyl ethyl ketone, methyl isopropyl ketone preferably acetone and acetonitrile. In one embodiment, the concentration of water miscible organic solvents are maintained below 25%, preferably 10%, more preferably 5% even more preferably free of organic solvent.

In another embodiment, the water concentration is maintained below 10%, preferably 5%, more preferably 1%, even more preferably free of water in water immiscible solvent system. In another embodiment the salt adsorbent is dry free of liquid.

The appropriate ratio of water and solvent can be obtained by addition or removal of solvents to have system for optimum formation compound-salt-adsorbent complex. The appropriate ratio of water and solvent can be obtained by addition or removal of solvents to have system for optimum formation of compound-salt-adsorbent complex. In another embodiment, another organic solvent is added, which decreases the polarity of the system. In such embodiement, the solvents are selected from but not limited to $C_{5-8}$ aliphatic alkanes such as heptane, hexane, cyclohexane or octane; $C_{6-8}$ aromatic hydrocarbons such as toluene.

Without wishing to be bound to any theory inventers believe that decreasing solvent content increases adsorption of compound with salt-adsorbent in aqueous system. In organic solvent system the increasing content of water decreases the adsorption of compound with salt-adsorbent.

Compound salt-adsorbent complex is then separated (step f) from the liquid for further processing.

The salt-compound absorbent obtained from the above said process is washed (step g) to remove bound impurities. The washing is performed using appropriate system, which removes the color and other impurities but not the compound of interest.

In one embodiment, the washing is performed using water or organic solvents or mixture thereof, in which the compound is less or not soluble. In such embodiment, the organic solvents are selected from but not limited to, $C_5$ to $C_8$ aliphatic alkanes, $C_6$ to $C_8$ aromatic hydrocarbons, $C_4$ to $C_8$ ethers and $C_3$ to $C_6$, ketones and acetonitrile.

In preferred embodiment, $C_{5-8}$ aliphatic alkanes are selected from heptane, hexane, cyclohexane or octane. In another preferred embodiment, $C_{6-8}$ aromatic hydrocarbons are selected from toluene & preferred $C_{4-8}$ ether is selected from diethyl ether, disopropyl ether, dibutyl ether. In preferred embodiment $C_{3-6}$ ester is selected from isobutyl acetate, n-butyl acetate, n-propyl acetate, isopropyl acetate or ethyl acetate. In most preferred embodiment, the non polar or weakly polar water immiscible organic solvent is ethyl acetate, iso butyl acetate, n-butyl acetate, isopropyl acetate and n-propyl acetate.

The above-described washing step is optional. The Echinocandin type compound may be eluted (step i) directly from compound-salt-adsorbent complex, but washing helps in improving quality of the desired product. Without wishing to be bound to any theory the applicants believe that the aqueous washing using water removes the polar impurities and non-polar solvent such as ethyl acetate washing removes the non-polar impurities. Hence, washing is the useful step for the removal of the both polar and non polar impurity.

In one embodiment, the suitable eluting system has superior affinity for Echinocandin-type compounds. The elution of Echinocandin-type compounds and preferably Pneumocandins is performed by using organic solvents which are selected from lower alcohols preferably ($C_1$-$C_6$) alcohols, in preferred embodiment, methanol n-butanol and isobutyl alcohol, dimethyl formamide, dimethyl sulfoxide, ketones preferably, methyl-ethyl ketone, acetonitrile and/or water mixture.

In such embodiment, the eluate is processed to obtain purified Pneumocandins by methods well known in prior art. In preferred embodiment, the eluate is concentrated under vacuum to obtain purified Pneumocandins. In such embodiment, acetonitrile and/or acetone are added to concentrate to precipitate the Pneumocandins. The precipitate is separated and dried to obtain purified Pneumocandins.

In one embodiment the present process carries out at 0° C. to 60° C. In preferred embodiment the present process carries out at 5° C. to 35° C. and in most preferred embodiment the process carries out at below room temperature.

The above adsorption of compound on salt-adsorbent complex formation step and elution can be performed more than once or repeated at any stream of purification process.

Following examples illustrate some of the preferred mode of carrying out the invention, including the best mode known to the inventors. These examples are provided for the purpose of illustration and should not be construed as limiting the scope of the invention.

Example 1

Isolation and Purification of Pneumocandin B0

13 L fermentation broth comprising Pneumocandin B0 and remaining soluble phosphates from medium components, in which, 260 gm of the calcium chloride solution is added. (100 g potassium phosphate may be added in case the medium is free of it). The mixture was stirred for 3 hrs. The solid cake was separated from aqueous medium by centrifugation or filtration. The filtrate substantially free of Pneumocandin was discarded. The compound from solid cake was extracted using 9 L methanol. The methanol extraction process was repeated. The methanol was separated from the solid cake by centrifugation and was evaporated in order to obtain aqueous concentrate. When 2 L of concentrate was obtained, salt adsorbent $CaPO_4$ was (100 g of $CaPO_4$, prepared by mixing Cacl2 and potassium phosphate solutions and neutralizing the solution; then filtering the precipitate obtained) added and stirred for 3 hrs. The mixture was concentrated under vacuum to obtained aqueous solution. The mixture was filtered to obtain the compound:salt-adsorbent complex. The obtained compound:salt-adsorbent complex was washed using water, thereafter, further it was washed using ethyl acetate. The purified compound was eluted from the salt adsorbent by using methanol. The elute was concentrated under vacuum to obtain purified Pneumocandin B0. The yield of the process is 70%. The concentrated Pneumocandin B0 was further precipitated using acetonitrile. The precipitate obtained is filtered and dried to obtain purified powder of Pneumocandin B0 having purity of more than 88% by HPLC analysis.

Example 2

Isolation and Purification of Pneumocandin B0

13 L fermentation broth comprising Pneumocandin B0 and remaining soluble phosphates from medium components, in which, 260 gm of the calcium chloride solution is added. (100 g potassium phosphate may be added in case the medium is free of it). The mixture was stirred for 3 hrs. The solid cake containing compound:salt adsorbent with mycelium were separated from aqueous medium by centrifugation or filtration. The compound from solid cake was extracted using 8 L iso-butyl alcohol (IBA). The iso butanol (IBA) extraction process is repeated using water saturated iso butanol (IBA). The isobutanol was separated from the solid cake by centrifugation and was evaporated under vacuum, in order to obtain concentrate. When approximately 3 L of IBA concentrate was obtained, the salt adsorbent (100 g of $CaPO_4$, prepared by mixing Cacl2 and potassium phosphate solutions and neutralizing the solution; then filtering the precipitate obtained) was added in concentrate and further concentration was continued to till the 500 ml of the IBA left. The compound:salt-adsorbent complex was obtained by filtering the remaining IBA. The obtained compound salt adsorbent complex was washed using water, thereafter, further it was washed using ethyl acetate. The purified compound was eluted from the salt adsorbent by using methanol. The eluate was concentrated under vacuum to obtain purified Pneumocandin B0. The yield of the process is 70%. The concentrated Pneumocandin B0 was further precipitated using acetonitrile. The precipitate obtained is filtered and dried to obtain purified powder of Pneumocandin B0 having purity of more than 88% by HPLC analysis.

Example 3

Isolation and Purification of Pneumocandin B0

14 L of fermentation broth comprising Pneumocandin B0 is extracted by iso butyl alcohol. The mycelial solids were separated by the filtration and extraction step with iso butyl alcohol was further repeated. The iso butyl alcohol was separated from the solid cake by filtration and was evaporated in order to obtain the concentrate. When approximately 3 L of IBA concentrate was obtained, the salt adsorbent (100 g of $CaPO_4$, prepared by mixing Cacl2 and potassium phosphate solutions and neutralizing the solution; then filtering the precipitate obtained) was added in concentrate and further concentration was continued to till the 500 ml of the IBA left. The obtained compound:salt adsorbent complex was washed using water, thereafter, further it was washed using ethyl acetate. The purified compound was eluted from the salt adsorbent by using methanol. The elute was concentrated under vacuum to obtain purified Pneumocandin B0. The yield of the process is 75%. The concentrated Pneumocandin B0 was further precipitated using acetonitrile. The precipitate obtained is filtered and dried to obtain purified powder of Pneumocandin B0 having purity of more than 89% by HPLC analysis.

Example 4

Purification of Crude Pneumocandin B0

10 g crude Pneumocandin B0 was dissolved in 70% methanol solution. 50 g of calcium phosphate was added and concentrated the mixture under vacuum to remove the solvent. The compound salt adsorbent was recovered by filtration. It was further washed by water and subsequently with ethyl acetate. The washing was performed till the color was found in the washing. The compound was eluted from the complex by using methanol. The elute was concentrated under vacuum and precipitated by the acetonitrile. The off white colored purified Pneumocandin B0 obtained.

Example 5

5 g crude Pneumocandin B0 was dissolved in 70% acetone solution. 25 g of calcium phosphate was added and concentrated the mixture under vacuum to remove the solvent. The compound salt adsorbent was recovered by filtration. It was further washed by water and subsequently with ethyl acetate. The washing was performed till the colour is found in the washing. The compound was eluted from the complex by using 90% acetone. The elute was concentrated under vacuum and precipitated by the acetonitrile to recover the compound. The off white coloured purified pneumocandin B0 obtained.

Example 6

5 g crude Pneumocandin B0 was dissolved in 70% acetonitrile solution. 25 g of calcium phosphate was added and concentrated the mixture under vacuum to remove the solvent. The compound salt adsorbent was recovered by filtration. It was further washed by water and subsequently with ethyl acetate. The washing was performed till the colour is found in the washing. The compound was eluted from the complex by using 88% acetonitrile. The elute was concentrated under vacuum and precipitated by the acetonitrile to recover the compound. The off white coloured purified pneumocandin B0 obtained.

Example 7

250 mg of each different insoluble phosphate salts of Fe, Cu, Ca, Zn, Mg, Mn were added in each 5 ml solution containing 100 mg of the crude Pneumocandin Bo. The solvent was evaporated under vacuum and the solution is centrifuged out to separate the salt—adsorbent. The compound is eluted from each salt adsorbent by using 10 ml methanol. The result of the experiment is summarized below in table 1.

| No. | Salt Adsorbent | Pneumocandin B0 (mg) In supenatent | Pneumocandin B0 (mg) In elute |
|---|---|---|---|
| 1 | $CaPo_4$ | 0.1 | 49 |
| 2 | $FePo_4$ | 0.95 | 35 |
| 3 | $ZnPo_4$ | 0.1 | 42 |
| 4 | $CoPo_4$ | 0.09 | 35 |

-continued

| No. | Salt Adsorbent | Pneumocandin B0 (mg) In supenatent | Pneumocandin B0 (mg) In elute |
|---|---|---|---|
| 5 | $CuPO_4$ | 0.3 | 39 |
| 6 | $MgPO_4$ | 0.09 | 41 |

We claim:

1. A process for the purification of lipopeptides comprising binding the lipopeptides on a salt adsorbent, wherein the salt adsorbent is prepared from phosphate and at least one cation and wherein the lipopeptides are of Echinocandin or Echinocandin type compounds.

2. The process as claimed in claim 1, wherein the cation is a divalent cation.

3. The process as claimed in claim 2, wherein the divalent cation is selected from $Ca^{+2}$, $Mg^{+2}$, $Fe^{+2}$, $Mn^{+2}$, $Cu^{+2}$, $Zn^{+2}$, and $Ba^{+2}$.

4. The process as claimed in claim 3, wherein the divalent cation is $Ca^{+2}$.

5. The process as claimed in claim 1, wherein the salt adsorbent is calcium phosphate.

6. The process as claimed in claim 1, wherein the salt adsorbent is copper phosphate.

7. The process for the purification of lipopeptides as claimed in claim 1 comprising the steps of:
    (a) treating an Echinocandin type compound with salt adsorbent in a suitable solvent system to obtain a salt adsorbent compound complex;
    (b) separating Echinocandin type compound salt adsorbent complex from the solvent system;
    (c) optionally, washing the separated Echinocandin type compound-salt adsorbent complex by using suitable washing system; and
    (d) eluting the desired compound from the adsorbent by using appropriate eluting system.

8. The process as claimed in claim 7 wherein the Echinocandin type compound is selected from Pneumocandins B0, A0, C0 and D0.

9. The process as claimed in claim 8, wherein the Echinocandin is Pneumocandin B0.

10. The process as claimed in claim 7, wherein the suitable solvent used in step (a), is water miscible, water immiscible or a mixture thereof.

11. The process as claimed in claim 10, wherein the suitable solvent system in step (a) comprises one or more of a fully aqueous system or C1-C6 lower alcohols; C2-C6 ketones and acetonitrile.

12. The process as claimed in claim 10 wherein the concentration of the water miscible solvent is maintained below 20%.

13. The process as claimed in claim 10, wherein the concentration of water immiscible solvent is maintained below 10%.

14. The process as claimed in claim 7, wherein the washing system used in step (c) is selected from water, and water immiscible solvents or a combination thereof.

15. The process as claimed in claim 7, wherein the eluting system used in step (d) is selected from one or more of dimethyl sulphoxide, dimethyl formamides, C1-C6 lower alcohols, C2-C6 ketones and acetonitrile.

16. The process as claimed in claim 1, further comprising preparing a synthetic product from the purified echinocandin type compound comprising the step of converting the purified echinocandin type compound to caspofungin, anidulafungin or micafungin.

17. The process as claimed in claim 14, wherein the washing system is selected from non polar or weakly polar water immiscible organic solvents selected from C5 to C8 aliphatic alkanes, C6 to C8 aromatic hydrocarbons, C4 to C8 ethers and C3 to C6 esters.

* * * * *